US005624946A

United States Patent [19]
Williams

[11] Patent Number: 5,624,946
[45] Date of Patent: Apr. 29, 1997

[54] USE OF LEFLUNOMIDE TO CONTROL AND REVERSE CHRONIC ALLOGRAFT REJECTION

[76] Inventor: James Williams, 655 Superior, Oak Park, Ill. 60302

[21] Appl. No.: 270,908

[22] Filed: Jul. 5, 1994

[51] Int. Cl.$^6$ ........................ A61K 31/42; A61K 31/275; A61K 31/535
[52] U.S. Cl. ........................ 514/378; 514/521; 514/236.8
[58] Field of Search ........................ 514/236.8, 378, 514/521

[56] References Cited

U.S. PATENT DOCUMENTS

| | | | |
|---|---|---|---|
| 4,087,535 | 5/1978 | Heubach | 514/378 |
| 4,284,786 | 8/1981 | Kammerer et al. | 548/248 |
| 4,351,841 | 9/1982 | Kammerer et al. | 424/272 |
| 4,636,513 | 1/1987 | Kammerer et al. | 514/326 |
| 4,965,276 | 10/1990 | Bartlett et al. | 514/378 |
| 5,268,382 | 12/1993 | Bartlett et al. | 514/378 |

FOREIGN PATENT DOCUMENTS

| | | |
|---|---|---|
| 2076555 | 2/1993 | Canada. |
| 2081173 | 4/1993 | Canada. |
| 4101324A1 | 7/1992 | Germany. |

OTHER PUBLICATIONS

Bartlett et al., "Development of Autoimmunity in MRL/lpr Mice and the Effects of Drugs on this Murine Disease," *Scand. J. Rheumatology*, S75:290–299 (1988).

Bartlett et al., "Leflunomide (HWA 486), a novel immunomodulating compound for the treatment of autoimmune disorders and reactions leading to transplantation rejection," *Agents Actions*, 32:10–21 (1991).

Bretzel et al., "Experimental Islet Transplantation in Small Animals," *Pancreatic Islet Cell Transplantation*, C. Ricardi, ed., R.G. Landis Co., Austin (1992).

Chong et al., "Leflunomide, a Novel Immunomodulatory Agent: In Vitro Analyses of the Mechanism of Immunosuppression," *Transplantation Proceedings*, 25:747–749 (1993).

Chong et al., "Leflunomide, a Novel Immunosuppressive Agent," *Transplantation*, 55:1361–1366 (1993).

Cosenza et al., "Combination Therapy with Brequinar Sodium and Cyclosporine Synergistically Prolongs Hamster–to–Rat Cardiac Xenograft Survival," *J. Heart Lung Transplantation*, 13:489–497 (1994).

Fontana et al., "Long–Term Follow–Up of Human Islet Autotransplantation," *Transplantation Proceedings*, 26:581 (1994).

Foster et al., "Leflunomide Immunosuppression in Rat Small Intestinal Transplantation," *Transplantation Proceedings*, 26:1599–1600 (1994).

Glant et al., "Immunomodulation of proteoglycan–induced progressive polyarthritis by leflunomide," *Immunopharmacology*, 23:105–116 (1992).

Hayry et al., "Chronic Allograft Rejection," *Immunological Reviews*, 134:33–81 (1993).

Horak et al., "T–lymphocyte interleukin 2–dependent tyrosine protein kinase signal transduction involves the activation of p56$^{lck}$," *Proc. Natl. Acad. Sci. USA*, 88:1996–2000 (1991).

Kahan et al., "Synergistic Interactions of Cyclosporine and Rapamycin to Inhibit Immune Performances of Normal Human Peripheral Blood Lymphocytes In Vitro," *Transplantation*, 51:232–239 (1991).

Kerckhaert et al., "Effects of Variation in Time and Dose of Cyclophosphamide Injection on Delayed Hypersensitivity and Antibody Formation," *Cellular Immunology*, 29:232–237 (1977).

Küchle et al., "Prevention of Kidney and Skin Graft Rejection in Rats by Leflunomide, a New Immunomodulating Agent," *Transplantation Proceedings*, 23:1083–1086 (1991).

Mattar et al., "Inhibition of the epidermal growth factor receptor tyrosine kinase activity by leflunomide," *FEBS Letters*, 334:161–164 (1993).

McChesney et al., "An Evaluation of Leflunomide in the Canine Renal Transplantation Model," *Transplantation*, 57:1717–1722 (1994).

Morris et al., "Inhibition of Arterial Intimal Thickening by Leflunomide: In Vivo Efficacy and Molecular Mechanisms," Presented at Annual Meeting of Am. Soc. Transplant Surgeons, May 20, 1994, Chicago, IL.

Ogawa et al., "Effects of Leflunomide on glomerulonephritis induced by antibasement membrane antibody in rats," *Agents Actions*, 31:321–328 (1990).

Ogawa et al., "Therapeutic Effects of Leflunomide, a New Antirheumatic Drug, on Glomerulonephritis Induced by the Antibasement Membrane Antibody in Rats," *Clinical Immunology Immunopathology*, 61:103–118 (1991).

Ono et al., "Improved technique of heart transplantation in rats," *J. Thoracic Cardiovascular Surgery*, 57:225–229 (1969).

Popovic et al., "Disease modifying activity of HWA 486 on the development of SLE in MRL/1–mice," *Ahents Actions*, 19:313–314 (1986).

(List continued on next page.)

Primary Examiner—Theodore J. Criares
Attorney, Agent, or Firm—Marshall, O'Toole, Gerstein, Murray & Borun

[57] ABSTRACT

The present invention relates to methods of controlling or reversing chronic rejection of allografts in a transplantation patient by administering leflunomide product alone, or in combination with one or more immunosuppressive agents selected from the group consisting of Cyclosporine A, FK506, rapamycin and corticosteroids. The invention also relates to methods of preventing or controlling acute and chronic rejection of xenografts in a transplantation patient by administering leflunomide product alone, or in combination with one or more immunosuppressive agents selected from the group consisting of Cyclosporine A, FK506, rapamycin and corticosteroids.

11 Claims, 3 Drawing Sheets

OTHER PUBLICATIONS

Schorlemmer et al., "Prolongation of Allogeneic Transplanted Skin Grafts and Induction of Tolerance by Leflunomide, a New Immunosuppressive Isoxazol Derivative," *Transplantation Proceedings*, 25:763–767 (1993).

Schwartz et al., "Drug–induced Immunological Tolerance," *Nature*, 183:1682–1683 (1959).

Stecher et al., "Disease Modifying Anti–Pheumatic Drugs", *Ann. Report Med. Chem.* 18:171–179 (1983).

Stockman et al., "Differential Effects of cyclophosphamide on the B and T Cell Compartments of Adult Mice," *J. Immunology*, 110:227–282 (1973).

Thoenes et al., "Leflunomide (HWA 486) Inhibits Experimental Autoimmune Tubulointerstitial Nephritis in Rats," *Int. J. Immunopharmacology*, 11:921–929 (1989).

Tilney et al., "Chronic Rejection—An Undefined Conundrum", *Transplantation*, 52:389–398 (1991).

Turk et al., "Further Studies on B–Lymphocyte Suppression in Delayed Hypersensitivity. Indicating a Possible Mechanism for Jones–Mote Hypersensitivity," 24:;751–758 (1973).

Ulrichs et al., "Suppression of Natural Xenophile Antibodies with the Novel Immunomodulating Drug Leflunomide" *Transplantation Proceedings*, 24:718–719 (1992).

Williams et al., "Immunosuppressive Effects of Leflunomide in a Cardiac Allograft Model," *Transplantation Proceedings*, 25:745–746 (1993).

Williams et al., "Leflunomide Based Immunosuppression in Rat Cardiac and Renal Xenotransplantation," Presented at Annual Meeting of the Am. Soc. Transplant Surgeons, May 20, 1994, Chicago, IL.

Williams et al., "Leflunomide and Cyclosporine in Rat Cardiac Transplantation", Presented at the 17th Annual Meeting of the Am. Soc. Transplant Surgeons, May 1992, Chicago, Illinois.

Williams et al., "Leflunomide in Experimental Transplantation," *Transplantation*, 57:1223–1231 (1994).

Xiao et al., "Leflunomide on Acute Rejection in Hamster to Rat Cardiac Xenografts," Presented at Second International Congress on Xenotransplantation, Sep. 26–29, 1993, Cambridge, England.

Xiao et al., "Effect of Leflunomide in Control of Acute Rejection in Hamster–to–Rat Cardiac Xenografts," *Transplantation Proceedings*, 26:1263–1265 (1994).

"Islet Autotransplantation: The Minnesota Experience," *Pancreatic Islet Cell Transplantation*, C. Ricardi, ed., R. G. Landis Co., Austin (1992).

Bouwman et al., "Experimental Xenotransplantation in Rodents—I: Skin Versus Heart Grafts," in *Xenotransplantation*, Cooper et al., eds, Springer–Verlag, Berlin (1991), pp. 323–329.

Cooper et al., "Introduction," in *Xenotransplantation*, Cooper et al., eds. Springer–Verlag, Berlin (1991), pp. 1–7.

Steinbruchel et al., "Experimental Xenotransplantation in Rodents–Total Lymphoid Irradiation, Cyclosporine, and Monoclonal Antibodies," *Xenotransplantation*, Cooper et al., eds. Springer–Verlag, Berlin (1991), pp. 331–338.

Thomas et al., "Immunobiology of Xenografting in Rodents," in *Xenotransplantation*, Cooper et al., eds. Springer–Verlag, Berlin (1991), pp. 139–160.

Van Den Bogaerde et al., "Immunosuppression in Xeontransplantation," in *Xenotransplantation*, Cooper et al., eds. Springer–Verlag, Berlin (1991), pp. 161–178.

London et al., "Islet Purification", *Pancreatic Islet Cell Transplantation..*, Camillio Ricordi, ed; RG Landis Co., Austin, TX, pp. 113–123 (1992).

Ricordi et al., "Islet Isolation Assessment", *Pancreatic Islet Cell Transplantation.*, Camillio Ricordi, ed; RG Landis Co., Austin, TX, pp. 132–142 (1992).

Williams et al., "Leflunomide, A Potent Immunosuppressive Molecule", International Conference on New Trends in Clinical and Experimental Immnosuppression, Geneva, Switzerland (Feb. 10, 1994).

Fig. 3

USE OF LEFLUNOMIDE TO CONTROL AND REVERSE CHRONIC ALLOGRAFT REJECTION

BACKGROUND OF THE INVENTION

Organ transplants of liver, kidney, heart and lung are now regularly performed as treatment for end-stage organ disease. Allograft (same species donor and recipient) as well as xenograft (different species donor and recipient) transplants have been performed. In 1989 over 14,000 patients received allografts in the United States alone. Transplant outcome has progressively improved with the development of refinements in tissue typing, surgical techniques, and more effective immunosuppressive treatments. However, because of problems with long-term chronic rejection, organ transplantation is not yet a permanent solution to irreversible organ disease.

Chronic rejection, which manifests as progressive and irreversible damage to the graft from attack due to host immune responses, is the leading cause of organ transplant loss after the first postoperative year. A significant proportion of grafts, regardless of type, deteriorate and fail within the first several months or years after transplant despite administration of maintenance immunosuppression. Although the pace of graft destruction varies from patient to patient, essentially all heart or kidney transplants of cadaveric origin eventually succumb to chronic rejection. This persistent rate of decline of long-functioning grafts has remained constant over time, despite improvements in immunosuppressive therapy and in overall care for graft recipients. The half-life of a kidney transplant after the first year is seven years and has not changed with use of Cyclosporine A or anti-lymphocyte antibodies. In multicenter data from North America reported in 1988, less than half of the kidney cadaveric grafts continued to function at six years post-transplant although 80% behave satisfactorily at the end of the first year. There is a similar rate of decline for other types of organ grafts; the incidence of coronary arteriosclerosis in heart grafts reaches 50% before five years, resulting in a 25% mortality rate, and 40–50% of liver allografts no longer function at 5 years after transplant. This somewhat lower rate of chronic rejection for liver may be due to lower immunogenicity of liver tissue.

The mechanism underlying chronic rejection is poorly understood. Various aspects of host immune responses have been implicated in the phenomenon, and its etiology may be multifaceted. Chronic rejection is inexorable and uncontrollable because there is no known effective treatment. Thus, there continues to exist a need for a treatment effective in preventing, controlling or reversing the chronic rejection of organ transplants.

The rejection of xenograft transplants, which involve the exchange of organs between animals of different species, occurs by a different mechanism than allograft rejection. Discordant xenotransplants result in immediate rejection within minutes to a few hours, produced by pre-existing antibodies and complement-mediated hyperacute rejection. Discordant combinations occur when organs are exchanged between species having wider phylogenetic separation, such as pig to dog and pig to primate. Concordant xenotransplants involve organ exchange between more closely related animals, such as mouse or hamster to rat, or chimpanzees or baboon to man. Concordant xenografts evoke an immune response which is quite different from the response to allografts. The differences include a more rapid antibody response which appears to be T-cell independent, and graft destruction through humoral attack on endothelial cells, producing parenchymal hemorrhage or vascular thrombosis. Mononuclear cell infiltration plays a minimal role in this accelerated rejection process. Because of the severely limited supply of transplantable human organs, the future of transplantation depends on the development of effective protocols for transplanting non-human organs to humans.

Organ transplants evoke a variety of immune responses in the host. In acute rejection, the graft is initially invaded by the host's mononuclear cells (macrophages, lymphocytes, and monocytes). If these cells perceive antigenic differences in the graft, they will process and present the antigen to a T-lymphocyte and activate it in an antigen specific manner. This T-cell then stimulates an immune response, which usually is a combination of cellular (T-cell mediated) and humoral (B-cell mediated) responses. These reactions appear to be the primary cause of the early acute rejection that may occur within the first six weeks after transplant. If untreated, acute rejection is a rapid and severe process that causes destruction of the transplant within a few days. In general, if the patient has not had an acute rejection within the first six weeks or if the patient has had a rejection that has been successfully treated, it is unlikely that a separate episode of acute rejection will occur provided that the patient continues standard immunosuppressive therapy.

Chronic rejection, on the other hand, is a gradual process of deterioration and failure that occurs later in the life of the transplant, from several months to several years. The dramatic histological picture of progressive cellular infiltration and allograft destruction that is seen with acute rejection is less pronounced in chronically rejected grafts. Little qualitative difference has been found between the cell populations that infiltrate acutely-rejecting, chronically rejecting and well-functioning allografts; in all cases, the cells consist primarily of T-lymphocytes, B-lymphocytes and macrophages.

Few investigators have examined the immunological mechanisms of chronic rejection. A review article by Tilney et al., *Transplantation*, 52:389–398 (1991) collects existing information on the chronic rejection process and attempts to place it in perspective with present knowledge of host immunity. The common denominator of the chronic rejection process is the development of obliterative fibrosis of hollow structures within the graft, regardless of whether they are blood vessels, bronchioles, or bile ducts. It is not known whether the changes seen in actual organ tissue are due to arterial insufficiency and progressive graft ischemia, or whether they are simply manifestations of subclinical host immunological attack.

The obstructive vascular lesion characteristic of chronic rejection appears to progress through repetitive endothelial injury induced by host antibody or antigen-antibody complexes and complement, through intimal proliferation, smooth muscle cell hypertrophy, repair, and finally to gradual luminal obliteration. In the first of these three stages, the vascular endothelium is damaged by host antibody or antigen-antibody complexes and complement. This causes collagen to be exposed. Platelets then adhere to and accumulate on the surface of the vessel, the clotting cascade is activated, and fibrin is deposited. Various factors such as thromboxanes, platelet-derived growth factor (PDGF), leukotrienes and platelet activating factors (PAF) are released, often by injured endothelial cells. Finally, macrophages and monocytes which are presumably attracted by PDGF migrate to the area, proliferate, and enter the surrounding tissues. PAF may promote these cells as well as increase the adherence of polymorphonuclear leukocytes to the vascular endothelium. Corresponding induction of PDGF receptors on vascular intima and smooth muscle cells renders these cells more sensitive to PDGF. Increased production of tumor necrosis factor (TNF), thromboxane A2, thromboxane B2, beta thromboglobulin, platelet factor 4, leukotrienes and prostaglandins are also seen and may be involved in the rejection process. Humoral, or antibody-based, immune response is also believed to play a role in chronic rejection because immunoglobulin and complement deposits have been shown in areas of intimal thickening. It has been shown that the development of intimal thickening can be reproduced histologically by intraarterial infusion of donor-specific antibodies.

For kidney grafts, after a long period of satisfactory and stable function, the patient begins to develop characteristic manifestations of glomerulosclerosis and nephrosclerosis: progressive proteinuria, hypertension, and declining kidney function. Histological findings are tubular atrophy, parenchymal fibrosis, and chronic arteritis. The most striking early changes involve enlarged glomeruli with amorphous capillary deposits under the basement membrane that are not immune complexes. Capillary lumina may be narrowed. In time, gradual functional deterioration appears, with fibro-obliterative arterial lesions and glomerular fibrosis. Damage to the vascular endothelium is a prominent feature. The end result is parenchymal fibrosis presumably due to progressive ischemia. Changes to the glomeruli are less consistent than the vascular changes and manifest as decreased size, folding and thickening of the capillary basement membrane, focal hyalinization and fibrosis. Deposits of fibrinogen, immunoglobulin, and complement often occur in peritubular capillaries.

In heart grafts, chronic rejection is characterized by diffuse fibrous intimal thickening of the arteries and arterioles. In contrast to naturally occurring arteriosclerosis, these lesions are usually concentric and affect the entire length of the vessel wall. Proximal intimal plaques that are indistinguishable from atherosclerosis in older individuals are sometimes seen. Histologically, these lesions show cellular proliferation with variable deposition of collagen, ground substance and lipid. These lesions are composed predominantly of smooth muscle cells, macrophages and T-cells. The consistent appearance of T-cells and macrophages and the deposition of immunoglobulin and complement in the affected vessel walls suggests that these lesions are due to an immune response. Later in the process, fibrotic changes may appear throughout the myocardial tissue. Clinically, the patient may develop congestive heart failure, myocardial infarction, ventricular arrhythmias and sudden death.

Chronic rejection of liver grafts develops in as many as half of the long-term recipients and contributes to about 20% of graft failure. Clinically, the patient gradually develops relatively asymptomatic cholestatic jaundice followed by increasing levels of serum bilirubin, alkaline phosphatase, and glutamyl transpeptidase. Unlike in acute early rejection, where bile ducts become distorted by infiltration of inflammatory cells and the epithelial cell changes involve both nuclei and organelles, the lesions in chronic rejection are characteristic focal destruction of the bile ducts, particularly involving the smaller interlobular bile ducts, and progressing in some cases to disappearance of these ducts. Arteriosclerotic-like changes occur in blood vessels, with arterial wall thickening causing vascular insufficiency. The larger branches of the hepatic artery often develop graft arteriosclerosis, myointimal proliferation, foam cell deposition, and intimal inflammation. Histologically, this obliterative arteriopathy is characterized by T-cell infiltration of the vessel walls, indicating that the lesion is immunological in nature.

For lung transplant patients, clinical symptoms of chronic rejection include gradually increasing shortness of breath and coughing, with decreased exercise tolerance. The chest X-ray is generally negative. A characteristic diffuse obstruction of terminal bronchioles occurs in as many as half of the longterm surviving recipients of heart-lung grafts. Histologically, the condition manifests with bronchiolar epithelial ulceration, peribronchial inflammatory infiltrate, and intraluminal plugs of mucus, with necrotic cells and granulation tissue. As the chronic process evolves, the infiltrates decrease and the bronchiolar openings become progressively obliterated by fibrosis. Arteriosclerotic changes are also noted in the small arteries and veins.

Leflunomide (HWA-486) is an isoxazole derivative with a chemical name of N-(4-trifluoromethylphenyl)-5-methylisoxazol-4-carboxamide. After administration, the compound is rapidly converted to its active open-ring form, N-(4-trifluoromethylphenyl)-2-cyano-3-hydroxycrotonamide(A771726). [Stecher et al., Ann. *Report Med. Chem.*, 18:171–179 (1983).]Leflunomide originated from a series of compounds that were designed as agricultural herbicides by scientists at Hoechst AG. It was later found to have anti-inflammatory and immunosuppressive activity, and it has been evaluated in animal models of autoimmune disease as well as in some animal models of transplant rejection. The drug is well tolerated in animals and man and is currently under clinical investigation in human patients with advanced rheumatoid arthritis.

U.S. Pat. No. 4,087,535 by Heubach describes a group of 5-methyl-isoxazole-4-carboxylic acid anilides having anti-inflammatory and analgesic activity. U.S. Pat. No. 4,351,841 by Kammerer et al. reports that the particular anilide leflunomide displays superior anti-inflammatory activity and decreased toxicity. In U.S. Pat. No. 4,351,841, leflunomide was shown to inhibit immunopathological processes in two rat adjuvant arthritis models and a rat allergic encephalitis model.

U.S. Pat. No. 4,965,276 by Bartlett et al. describes the use of leflunomide to treat chronic graft vs. host (cGvH) disease and other autoimmune diseases such as systemic lupus erythematosus (SLE). Graft vs. host disease is characterized by an immune reaction that originates from the graft and is directed against host tissue. It thus differs from the rejection of a graft by the host, which involves a host immune response directed against the graft. Features of the acute GvH reaction are spleen and liver enlargement, lymph node hypertrophy, hemolytic anemia, low levels of immunoglobulins and complement, and diminished immunological reactivity. The chronic form of this disease process produces symptoms that very closely resemble those of SLE and include lymphadenopathy, immune complex glomerulonephritis and formation of numerous antibodies.

In U.S. Pat. No. 4,965,276, leflunomide and its metabolite were tested in a mouse cGvH disease model, in which an SLE-like condition was induced by initiating a cGvH reaction with two injections of spleen and thymus cells, and in MRL-lpr/lpr mice, which spontaneously develop a severe autoimmune disease that has features similar to human SLE and rheumatoid arthritis. Either leflunomide or its metabolite were effective in inhibiting the development of cGvH disease or SLE. Both compounds prevented development of glomerulonephritis, reduced anti-dsDNA titer, decreased the GvH index (a measure of relative spleen enlargement), and improved the diminished proliferative ability of T-lymphocytes.

In other experiments using MRL/lpr mice, leflunomide has been found to be equal or superior to Cyclosporine A (CsA) in ability to inhibit SLE. [Popovic et al., *Agents Actions*, 19:313–314 (1986)]. Treatment with leflunomide stops disease progression and prevents the development of glomerulonephritis. Leflunomide also suppresses the intense accumulation of lymphocytes in the lymph nodes and spleen of these mice, restores the T-cell helper/suppressor ratio to normal values, and restores the depressed proliferative response of lymphocytes and macrophages. Leflunomide in a different experiment was also effective in treating mice that had elevated levels of protein in their urine, indicative of progression to kidney damage. [Bartlett et al., *Scand. J. Rheumatol.*, 75:290–299 (1988)]. At the end of 10 weeks, 90% of the animals receiving leflunomide were still alive compared to 40% of the animals that received Cyclosporine A or prednisolone.

Leflunomide has also been tested in rat models of tubulointerstitial nephritis. Thones et al., *Int. J. Immunopharmacol.* 11:921–929 (1989) reported that leflunomicte was very effective in Brown-Norway (BN) rats in preventing experimental tubulointerstitial nephritis induced by immunization with tubular basement membrane in Freund's complete adjuvant. Leflunomide was as effective as Cyclosporine A, and was more effective than prednisolone, naproxen or indomethacin in preventing disease development. Leflunomide was also much more effective than any of the other drugs in reducing the incidence of autoantibody formation. In another model, Ogawa et al., *Agents Actions* 31:321–328 (1990), showed leflunomide to be effective in both preventing and curing glomerulonephritis induced in Sprague-Dawley rats by injection of anti-basement membrane antibody. An oral dose of 2 mg/kg/day of leflunomide, administered prophylactically (starting 2 days before disease induction and ending on day 20) or therapeutically (starting 5 days after disease induction and ending on day 20) led to a significant decrease in total urinary protein, plasma cholesterol and fibrinogen, as well as decreased deposition of fibrin, immunoglobulin G and complement C3.

In a BALB/c mouse model of proteoglycan-induced arthritis, Glant et al., *Immunopharmacol.*, 23:105–106 (1992) showed that leflunomide suppresses acute inflammation and protects animals from new inflammatory episodes or acute exacerbation of chronically inflamed joints. If untreated, the arthritis leads to progressive deformities, ankylosis and the loss of articular cartilage.

In in vitro studies, leflunomide metabolite (A771726) has been observed to inhibit murine B-cell and T-cell proliferation, with the drug being a more potent inhibitor of B-cell proliferation. [Bartlett et al., *Agents Actions*, 32:10–21 (1991).]Leflunomide has also been shown to inhibit human T-cell proliferation stimulated by (1) allogeneic lymphocytes, (2) anti-CD3 or anti-CD28 monoclonal antibodies in combination with phorbol myristate acetate (PMA), or (3) IL-2 or IL-2 with PMA. [Chong et al., *Transplant. Proc.*, 25:747–749 (1993).]Leflunomide only partially inhibits the production of IL-2. It appears to function by blocking IL-2 signal transduction, possibly by inhibition of protein-tyrosine tyrosine kinase activity. [Horak et al., *Proc. Nat'l. Acad. Sci.* (USA), 88:19962000 (1991).] Leflunomide is capable of inhibiting epidermal growth factor (EGF)-dependent cell growth by a mechanism that also appears to involve inhibition of tyrosine-specific protein kinase activity; leflunomide inhibits the intrinsic EGF receptor kinase as well as other kinases such as platelet derived growth factor-receptor (PDGFR) tyrosine kinase activity. [Matter et al., F.E.B.S., 334:161–164 (1993).]

Leflunomide has been evaluated for its ability to prevent rejection of skin (non-vascularized organ), kidney, small intestine and heart transplants in rats, and kidney transplants in dogs. Leflunomide has also been evaluated for its effect on chronic rejection of heart and femoral arterial grafts in rats and heart grafts in monkeys. The combination of leflunomide and Cyclosporine A has been evaluated for potential to prevent rejection of skin, heart and kidney transplants, and to reverse acute rejection of heart transplants.

In one study, Lewis (LEW) rats received skin grafts from DA rats or F344 rats received skin grafts from LEW rats. Graft rejection usually occurs at about 9–10 days (DA-LEW) or 15–16 days (LEW-F344). Leflunomide administered by gavage at doses ranging from 2.5 to 20 mg/kg for 10 days more than doubled graft survival time compared to untreated animals. [Kuchle et al., *Transplant. Proc.*, 23:1803–1806 (1990).]In later studies, combined treatment with CsA orally at 25 mg/kg and leflunomide at 5 mg/kg for 20 days resulted in long-term graft survival (>50 days) for 50% of the animals, in both models. Delayed treatment with leflunomide, but not with CsA, achieved prolongation of skin graft survival, even when started five to ten days after grafting. [Schorlemmer et al., *Transplant. Proc.*, 25:745–746 (1993).]

Kuchle et al., supra, also tested leflunomide in a BN-LEW renal transplant model of acute rejection in which both of the recipient's kidneys are removed at the time of transplantation. Untreated allograft recipients cease urine production and die at about eight days after transplantation. Treatment with leflunomide at 5 or 10 mg/kg/day by gavage for 30 days prolonged survival to more than 60 days. These results were very similar to the protection attainable with CsA treatment, whereas neither azathioprine nor prednisolone offered any protection.

Leflunomide was studied in a BN-LEW rat model of heterotopic small intestinal transplantation, in which the recipient's native bowel is left intact and the graft mesenteric vein is anastomosed to the vena cava. [Foster et al., *Transplant. Proc.*, 26:1599–1600 (1994).]Reconstruction of mesenteric venous drainage via the portal vein was required in order for leflunomide to be effective. Treatment with leflunomide metabolite (A771726) at 5 mg/kg/day by gavage for 7, 14 and 28 days prolonged the survival of recipients to 15.0±2.1, 21.2±1.6 and 33.8±2.4 days from 9.7±1.0 days in no-treatment controls. The effect of leflunomide was substantially improved by administering the drug via continuous infusion pump, which resulted in prolongation of survival to 29.3±13.8 and 38.8±11.5 days, after 7 and 14 days of treatment, respectively.

The ability of leflunomide alone or in combination with Cyclosporine A to prevent acute rejection was further studied in a BN-LEW heterotopic cardiac transplant model of acute rejection. [Williams et al., *Transplant. Proc.*, 25:745–746 (1993).]Abdominal-heterotopic cardiac transplants (grafting of the heart into the recipient's abdomen) were performed in 122 LEW rats, and acute rejection was diagnosed by cessation of palpable heartbeat in the cardiac allograft. Leflunomide at doses ranging from 0.63 to 10 mg/kg/day given for 7 days significantly prolonged graft survival compared to controls. When the rats were treated for 21 days at a dose of 5 mg/kg/day, indefinite graft survival (>100 days) occurred in three of six animals receiving leflunomide but in none of the 21-day CsA-treated animals.

The combination of CsA and leflunomide resulted in a significant improvement of graft survival compared to the use of either drug alone, and a synergistic effect was observed at low doses of both drugs (leflunomide at 0.31 mg/kg/day combined with CsA at 1.25 mg/kg/day) as determined by the Cox Stepwise Proportional Hazard Model. These additive or synergistic effects were determined not to be due to reduced drug elimination.

The ability of leflunomide to reverse established acute rejection was also explored in the BN-LEW heterotopic cardiac transplantation model. [Williams et al., *Transplantation*, 57:1223–1231 (1994) (presented at Am. Soc. Transplant Surg. meeting, May 28, 1992, Chicago, Ill.).]In this model, mononuclear leukocyte infiltration is histologically evident in the allograft by day 4; by day 6, myocyte necrosis is well established, and by day 7, rejection is complete. When treatment was started on the day of transplantation, a 7- or 14-day course of leflunomide or CsA at 5 mg/kg by gavage produced approximately equal prolongations of survival. When treatment was started 4 or 6 days post-transplantation, after acute rejection is established, leflunomide treatment for 7 days significantly prolonged the mean survival time of the cardiac allografts to 25.4±1.4 days (when started at day 4) and 16.3±8.5 days (when started at day 6). Leflunomide when started at day 4 completely cleared the mononuclear leukocyte infiltration on histological analysis. Leflunomide was thus effective in reversing acute rejection as determined by both functional and histological criteria. These beneficial effects were not obtained with CsA therapy posttransplantation. Leflunomide treatment initiated on day 4 post-transplant also inhibited production of allospecific cytotoxic antibodies, which are primarily of the IgM isotype, causing an abrupt drop to near background levels after 7 days of treatment. The generation of allospecific IgG response was inhibited as well. The titres of allospecific antibodies gradually increased upon cessation of leflunomide treatment on day 11. In contrast, CsA begun on day 4 did not reduce cytotoxic antibody production, and had no effect on the titres of allospecific IgM and IgG in rats undergoing acute rejection.

Leflunomide alone and in combination with CsA was also evaluated in a canine renal transplantation model of acute rejection. Renal transplantation was performed on 30 female mongrel dogs, in which both kidneys were removed and replaced with an allogeneic kidney graft from a non-litter mate donor. Increasing doses of leflunomide with and without CsA were administered daily until death of the animal to determine the dose dependent effect of the drug. Leflunomide at 8 mg/kg and 16 mg/kg significantly improved survival from 9±1 days to 27±1 days (p=0.01 by Breslow test) and 21±2 days (p=0.002), respectively. Treatment with a combination of non-therapeutic doses of leflunomide and CsA (4 mg/kg leflunomide and 10 mg/kg CsA) resulted in all dogs surviving ≧30 days with normal renal function, with a mean graft survival of 61±15 days. In this combination-treated group, leflunomide was withdrawn from two dogs after 100 days; both progressed to rejection within 14 days. The use of leflunomide for canine treatment is limited, however, by toxicity due to the canine's N-acetylation enzyme deficiency.

Leflunomide has recently been shown to significantly inhibit intimal thickening in cardiac allograft coronary arteries, femoral arterial grafts, and balloon-injured native carotids. [Morris et al., "Inhibition of Arterial Intimal Thickening by Leflunomide: In Vivo Efficacy and Molecular Mechanisms", Am. Soc. Transplant Surg. meeting, May 20, 1994, Chicago, Ill.]For cynomolgus monkey recipients of heterotopic heart transplants, oral leflunomide treatment at varying doses of 15 to 50 mg/kg/day prolonged graft survival time in a dose-dependent manner to between 35 and 130 days, compared to a control mean survival time of 10 days. For LEW rat recipients of BN heterotopic heart grafts, grafts analyzed on day 50 from rats treated orally with 15 mg/kg/day leflunomide had no graft vascular disease, and the rats' sera contained no antibodies directed against the BN grafts. For LEW recipients of BN orthotopic femoral arterial grafts, oral leflunomide treatment (10 mg/kg/day) resulted in reduced intimal thickening compared to untreated controls. Leflunomide (20 mg/kg daily from day 3 pre-transplant to day 13 post-transplant) also significantly reduced intimal thickening in balloon-injured carotids.

Of interest to the present invention is the finding that leflunomide is capable of suppressing the production of natural and induced antibodies to xenoantigens. [Ulrichs et al., *Transplant. Proc.*, 24:718–719 (1992).]Rats that received 10 mg/kg/day of leflunomide for 10 days showed a decrease in preexisting, natural xenophile antibodies to human peripheral blood lymphocytes (PBL). In rats sensitized with a single intraperitoneal injection of human PBL antigen, treatment with leflunomide at a dose of 3 or 10 mg/kg/day from day −4 to day +10 inhibited xenophile antibody production in a dose-dependent manner. Antibody reactivity rises again when leflunomide treatment is terminated.

SUMMARY OF THE INVENTION

The present invention provides methods for controlling and reversing chronic rejection of transplanted allografts after chronic rejection is established, and methods for preventing or controlling acute or chronic rejection of transplanted xenografts, by administering leflunomide product alone or in combination with another immunosuppressive agent or agents selected from the group consisting of Cyclosporine A, FK506, rapamycin and corticosteroids. The invention is based on the surprising discovery that, in treatment initiated after signs of chronic rejection have appeared, leflunomide product alone is capable of arresting the progression of chronic rejection, and the combination of leflunomide product and Cyclosporine A is capable of reversing chronic rejection. The invention is also based on the unexpected discovery that leflunomide product alone can prolong xenograft survival, and leflunomide product in combination with Cyclosporine A has the ability to completely prevent chronic xenograft rejection.

According to one aspect of the invention, a method is provided for controlling or reversing chronic rejection in a transplantation patient by administering to a patient suffering from chronic rejection of an allograft a therapeutically effective amount of leflunomide product alone, or in combination with therapeutically effective amounts of one or more immunosuppressive agents selected from the group consisting of Cyclosporine A, FK506, rapamycin and corticosteroids. The leflunomide product can be administered to humans in doses ranging from 0.1 mg to 80 mg daily, varying in children and adults, or in equivalent doses at longer intervals. In the combinative therapy, Cyclosporine A can be administered at doses from 0.1 to 12 mg/kg daily, FK506 at doses from 0.05 to 2 mg/kg daily, rapamycin at doses from 0.05 to 5 mg/kg daily, and corticosteroids at doses of 0.1 to 0.5 mg/kg daily, with doses for each drug varying in children and adults.

Another aspect of the invention provides a method of preventing or controlling acute or chronic rejection in a xenograft transplantation patient comprising administering to a patient receiving a xenograft a therapeutically effective amount of leflunomide product alone, or in combination with therapeutically effective amounts of one or more immunosuppressive agents selected from the group consisting of Cyclosporine A, FK506, rapamycin and corticosteroids.

Another aspect of the present invention involves the use of leflunomide product (HWA-486 and/or A771726), alone, or in combination with one or more immunosuppressive agents selected from the group consisting of Cyclosporine A, FK506, rapamycin and corticosteroids, in the manufacture of a medicament for controlling or reversing chronic allograft rejection and/or for preventing or controlling acute or chronic xenograft rejection.

Numerous additional aspects and advantages of the invention will become apparent to those skilled in the art upon consideration of the following detailed description of the invention which describes presently preferred embodiments thereof.

DETAILED DESCRIPTION

Leflunomide products have previously been shown to prevent acute rejection of skin, heart, intestinal and kidney allografts in rats and kidney allografts in dogs. Experiments in the BN-LEW rat cardiac transplantation model have shown that the drug can reverse functional and histological signs of well-established acute rejection, and can reduce titres of circulating allospecific cytotoxic antibodies. Leflunomide products are chemically unrelated to any other immunosuppressive drug currently in use, and studies suggest that leflunomide's mechanism of action differs from that of other immunosuppressive drugs such as Cyclosporine A, FK506, rapamycin, azathioprine, corticosteroids, antilymphocyte globulin and OKT3.

The rate of allograft loss due to chronic rejection has not changed over time in spite of improved immunosuppressive therapy and improvements in overall care of graft recipients. Once chronic rejection is established, there is no currently used treatment that can alter its progress. The present invention provides methods for controlling and reversing chronic rejection of allografts by administering leflunomide product alone or in combination with Cyclosporine A. The invention is based on the surprising discovery that, in a rat model of chronic rejection, leflunomide treatment initiated after histological signs of chronic rejection have appeared is capable of arresting the progression of chronic rejection. In this model, the combination of leflunomide product and Cyclosporine A is uniformly capable of reversing chronic rejection, returning vascular histology changes to near normal. No single drug or combination drug therapy has been previously reported to reverse the vascular changes of chronic rejection in a well controlled study.

According to one aspect of the invention, a method is provided for controlling or reversing chronic rejection in a transplantation patient by administering to a patient suffering from chronic rejection of an allograft a therapeutically effective amount of leflunomide product. The leflunomide product can be administered to humans at doses ranging from 0.1 to 80 mg daily, varying in children and adults, or more preferably at doses ranging from 15 to 60 mg daily for adults. Equivalent dosing of leflunomide product can be administered at longer intervals, e.g. larger doses once or twice weekly, due to the longer half-life of 2–5 days of leflunomide product in humans. The therapeutically effective dose may be adjusted to provide maximum reduction in the vascular lesions and obstructive fibrosis characteristic of chronic rejection, without resulting in excessive toxicity. In animal studies, extremely high doses of leflunomide result in liver and cardiac toxicity. In humans, a side effect of accumulation of the metabolite trifluoromethyl aniline is a Heinz-body hemolytic anemia; the appearance of anemia in a patient thus may be an early, sensitive sign of adverse side effects due to leflunomide product administration and an index of adequacy of drug dosing.

This aspect of the invention may also be practiced by administering leflunomide product in combination with therapeutically effective amounts of one or more immunosuppressive agents selected from the group consisting of Cyclosporine A, FK506, rapamycin and corticosteroids. The combination of leflunomide product and Cyclosporine A has been demonstrated to exert synergistic immunosuppressive effects on acute rejection using the Cox Stepwise Proportional Hazards model of analysis, and is also shown herein to provide reversal of chronic rejection.

In the leflunomide/CsA combination treatment, leflunomide product can be administered to humans in doses ranging from 0.1 to 80 mg daily (or equivalent dosing at longer intervals), varying in children and adults, and CsA can be administered to humans in doses ranging from 0.1 to 12 mg/kg daily, varying in children and adults. In this combination, leflunomide product blocks signaling of cytokines such as IL-2, IL-4 and PDGF, and CsA reduces synthesis or release of cytokines such as IL-2. FK506 has the same mechanism of action as Cyclosporine A, i.e. reducing IL-2 production by blocking IL-2 gene transcription, and may be administered in doses ranging from 0.05 to 2 mg/kg daily, varying in children and adults. The combination of leflunomide and rapamycin is shown herein to result in additive or synergistic effects in vitro. Rapamycin can be administered in doses ranging from 0.05 to 5 mg/kg daily, varying in children and adults. Corticosteroids are believed to exert their effect by lowering production of IL-1, an action that is complementary to that of leflunomide product, and may be administered in doses ranging from 0.1 to 0.5 mg/kg daily, varying in children and adults. The therapeutically effective doses of all of these drugs, including leflunomide, in the combinative therapy will be lower than the usual doses of each drug used for single drug monotherapy.

Another aspect of the present invention provides methods for preventing or controlling acute or chronic rejection of transplanted xenografts, by administering leflunomide product alone or in combination with one or more immunosuppressive agents selected from the group consisting of Cyclosporine A, FK506, rapamycin and corticosteroids. This aspect of the invention is based on the unexpected discoveries that, in a hamster to rat concordant xenotransplantation model, leflunomide product alone can prolong heart or kidney xenograft survival, and leflunomide product in combination with Cyclosporine A can completely prevent chronic rejection of heart or kidney xenografts, resulting in essentially normal histology at 90 days after transplantation. No other single drug or combination of drugs has permitted long-term survival in the hamster to rat renal xenograft transplant model.

Specifically, this aspect of the invention provides a method of preventing or controlling acute or chronic rejection in a xenograft transplantation patient comprising administering to a patient receiving a xenograft a therapeutically effective amount of leflunomide product alone. Leflunomide product monotherapy may be administered at doses ranging from 0.1 to 80 mg daily, varying in children or adults, or in equivalent dosing at longer intervals. The invention also provides a method of preventing or controlling xenograft rejection by administering leflunomide in combination with therapeutically effective amounts of one or more immunosuppressive agents selected from the group consisting of Cyclosporine A, FK506, rapamycin and corticosteroids. In the combinative therapies, leflunomide product may be administered at doses ranging from 0.1 to 80 mg daily, or in equivalent dosing at longer intervals, while Cyclosporine A can be administered at doses from 0.1 to 12 mg/kg daily, FK506 at doses from 0.05 to 2 mg/kg daily, rapamycin at doses from 0.05 to 5 mg/kg daily, and corticosteroids at doses of 0.1 to 0.5 mg/kg daily, with doses for each drug varying in children and adults. The therapeutically effective doses of all of these drugs, including leflunomide product, in the combinative therapy will be lower than the usual doses of each drug in monotherapy.

The term "leflunomide product" as used herein means leflunomide, N-(4-trifluoromethylphenyl)-5-methylisoxazol-4-carboxamide (HWA-486), or its active metabolite, N-(4-trifluoromethylphenyl)-2-cyano-3-hydroxycrotonamide (A771726), or other derivatives or metabolites thereof that retain all or part of the immunosuppressive activity of leflunomide. Such products can be prepared by methods including those described in U.S. Pat. Nos. 4,087,535, 4,351,841 and 4,965,276.

A treatment capable of preventing acute rejection is a treatment that prevents the occurrence of functional or histological signs of acute rejection, when initiated on the day of transplantation or shortly thereafter, but before acute rejection has commenced. Similarly, a treatment capable of preventing chronic rejection is a treatment that prevents the occurrence of functional or histological signs of chronic rejection, when initiated before chronic rejection has commenced.

A treatment capable of controlling acute or chronic rejection is a treatment that slows the progression of the disease process, when initiated after functional or histological signs of acute or chronic rejection, respectively, are observed. A treatment capable of reversing acute or chronic rejection is a treatment that, when initiated after functional or histological signs of acute or chronic rejection (respectively) have appeared, reverses the disease process and returns clinical and histological findings closer to normal.

The methods of the present invention for controlling or reversing chronic rejection of allografts can be used to treat patients receiving skin, heart, lung, kidney, liver, pancreatic islet cells, or other allografts, or combination allografts such as heart-lung, etc. The methods of the present invention for preventing or controlling rejection of xenografts may be used to treat patients receiving skin, heart, lung, kidney, liver, bone marrow, pancreatic islet cells, or other xenografts, or combination xenografts such as heart-lung, etc. The methods of the present invention can be used with other current standard posttransplantation care, including antibiotics and other immunomodulatory therapy.

Either leflunomide product or Cyclosporine A may be administered systemically via, e.g., oral, intravenous, intramuscular or subcutaneous routes. The drugs may be aerosolized for pulmonary administration or administered intravenously via a continuous infusion pump. The drugs may also be administered topically via, e.g., ointment or patch. For the combination treatments, leflunomide product and Cyclosporine A can be administered simultaneously or sequentially.

Other aspects and advantages of the present invention will be understood upon consideration of the following illustrative examples. Example 1 relates to the effects of post-transplantation leflunomide therapy alone or in combination with Cyclosporine A on chronic rejection in rat cardiac allografts. Example 2 shows the effects of leflunomide alone or in combination with Cyclosporine A on acute and chronic rejection of concordant (hamster to rat) cardiac xenografts. Example 3 relates to the effects of leflunomide alone or in combination with Cyclosporine A on acute and chronic rejection of concordant (hamster to rat) renal xenografts. Example 4 relates to the effects of leflunomide in combination with rapamycin on lymphocyte proliferation in a one-way mixed lymphocyte reaction.

EXAMPLE 1

Effects of Leflunomide Alone or With Cyclosporine A on Chronic Rejection of Rat Cardiac Allografts This experiment explored the ability of leflunomide alone or in combination with Cyclosporine A (CsA) to control or reverse chronic rejection or rat cardiac allografts in a modification of the model described by Adams et al., *Transplantation*, 53:1115 (1992). In this model, F-344 rats are briefly treated with CsA upon receiving heart allografts from Lewis (LEW) rats. These rats share major histocompatibility antigens but differ at minor histocompatibility loci. A short course of immunosuppression results in a slow chronic rejection that gradually destroys the graft, with the appearance of reproducible histology similar to the chronic rejection seen in humans.

In this study, adult male LEW and F-334 rats (Harlan Sprague Dawley, Indianapolis, Ind.) were housed and fed according to National Institute of Health (NIH) guidelines. Donor and recipient animals were anesthetized with Ketamine/Xylazine (Fort Dodge, Iowa) 100/5 mg/kg. Fifty-eight F-344 rats underwent heart transplantation from LEW rats according to the modified technique of Ono et al., *Cardiovasc. Surg.*, 57:225 (1969), and were treated with CsA at 2 mg/kg for 5 days starting on the day of transplantation. Recipients that rejected the allografts before 90 days (5 of 58) were excluded from the experiment. Cardiac allograft survival was determined by daily abdominal palpation, and rejection was considered complete upon cessation of heart beat.

The three control groups were given no treatment and were sacrificed at designated 30-day intervals to observe the development of chronic rejection. The treatment groups were administered daily doses of leflunomide or leflunomide and CsA according to Table 1 below, beginning at day 30 and continuing to day 60 or day 90. CsA in oral form (Sandimmune, Sandoz Corporation, East Hanover, N.J.) was administered at 2, 5 or 10 mg/kg to rats by gavage. Leflunomide in its powder form (HWA-486, Hoechst AG, Germany) was suspended in 1% carboxymethylcellulose and administered at 5 or 10 mg/kg/day by gavage.

Upon sacrifice, the heart allograft was removed, serially sectioned into approximately 2-mm slices, and fixed in 10% buffered formalin overnight. The sections were embedded in paraffin and stained with hematoxylin and eosin, Verhoeff's elastin stain and Masson's trichrome stain to evaluate pathologic changes and to score graft arterial intimal thickening. The remaining sections were immunostained using standard indirect avidin-biotin techniques (Vectastain ABC-Elite, Vector Laboratories, Burlingame, Calif.) with monoclonal antibodies against smooth muscle actin (DAKO, Carpin Terra, Calif.) to evaluate intimal smooth muscle proliferation, and with polyclonal antibodies against phosphotyrosine to evaluate tyrosine kinase activity by counting phosphotyrosine positive cells. Anti-donor specific IgM and IgG titres in serum were determined by flow cytometry as described previously in Williams et al., *Transplantation*, 57:1223–1231 (1994). Allospecific antibody titres among the groups were compared using the unpaired Student's t-test.

The sections were examined by light microscopy, and 20 to 70 arteries in each allograft were blindly scored for severity of arterial intimal thickening according to the general standard of Adams et al., supra, using the following histological scores: a score of 0 was a normal artery; a score of 1, intimal thickening up to approximately 50% of the perimeter of the vessel, with less than 20% luminal compromise; a score of 2, intimal thickening involving between 50% and 100% of the perimeter of the vessel, with less than 20% luminal compromise; score of 3, circumferential intimal thickening, with more than 20% but less than 50% luminal compromise; score of 4, circumferential intimal thickening, with more than 50% but less than 80% luminal compromise; score of 5, circumferential intimal thickening, with more than 80% luminal compromise. The mean histologic scores for each control or treatment group are displayed in Table 1 below. Statistical comparisons of histological scores were performed using the Mann-Whitney U - Wilcoxon Rank Sum W Test.

The three control groups were observed for development of progressive chronic rejection. Histologic characteristics of chronic allograft rejection included mononuclear cell infiltration and proliferation of smooth muscle cells and fibroblast-like cells, which may be limited to the intima or may involve all layers of the artery. Fibrotic intimal thickening was readily observed in long-term surviving allografts. The animals in group 1 (n=6) were sacrificed on day 30; their mean vascular histologic score was $2.33\pm0.88$. In this group, arterial intimal thickening was dominated by mononuclear cell infiltration with edema, combined with a small amount of actin-positive smooth muscle cell proliferation. The animals in group 2 (n=6) were sacrificed on day 60; their mean vascular histologic score was $2.71\pm1.33$. In this group, the arterial intimal thickening was now dominated by smooth muscle cell proliferation. Mononuclear cell infiltration was also prominent. The animals in group 3 (n=6) were sacrificed on day 90; their mean vascular histologic score increased to $3.35\pm0.91$. In this group, the arterial intimal thickening was dominated by smooth muscle and fibroblast-like cell proliferation. A progressive arterial chronic injury was observed. Examination of heart tissue among the three groups revealed severe mononuclear cell infiltration of myocardium in group 1, which was gradually reduced in groups 2 and 3, and was associated with mild to moderate myocardial fibrosis. This system clearly displays a progression of chronic arterial injury over the course of the rejection.

Different treatment regimes were tested in this chronic rejection model, according to Table 1 below. When CsA at 5 mg/kg was begun on day 30 (group 4), the condition of arterial intimal thickening did not significantly improve by day 60; this group had a mean histologic score of $1.61\pm0.83$ (p=0.229 vs. control on day 60). Even when the dosage of CsA was increased to 10 mg/kg from day 60 (group 7), the process of arterial intimal thickening progressed by clay 90 to a mean score of $2.81\pm0.97$, with increasing smooth muscle proliferation. Moderate to severe myocardial mononuclear cell infiltration and mild to moderate myocardial fibrosis were observed. Although CsA temporarily slowed the progression of chronic rejection, continued CsA treatment was unable to sustain this effect; by 90 days the CsA-treated group scores were statistically unchanged from the untreated control group. CsA treatment thus was unable to halt or reverse the chronic rejection process.

When leflunomide at 5 mg/kg was begun on day 30 (group 5), arterial intimal thickening did not significantly improve by day 60; this group had a mean histologic score of $1.55\pm0.53$ (p=0.078 vs. control on day 60). After the dosage of leflunomide was doubled to 10 mg/kg on day 60 (group 8), the arterial intimal thickening was significantly inhibited, with less severe smooth muscle proliferation; for this group, the mean score was $1.38\pm0.92$ by day 90 (p=0.0176 vs. control on day 90). Interstitial mononuclear cell infiltration and myocardial fibrosis were mild. These results show that leflunomide at 10 mg/kg was able to halt the progression of chronic rejection and partially reverse the process of arterial thickening.

When the combination therapy of leflunomide at 5 mg/kg and CsA at 5 mg/kg began on day 30 (group 6), arterial intimal thickening was significantly ameliorated by day 60, with a mean histologic score of $0.80\pm0.25$ (p=0.01 vs. control on day 30, p<0.016 vs. control on day 60). Combination therapy was also superior to monotherapy with either leflunomide (p<0.01) or CsA (p<0.05). When both dosages of leflunomide and CsA were doubled to 10 mg/kg at day 60 (group 9), the control of arterial intimal thickening was sustained, with a mean score of $0.68\pm0.38$ (p<0.004 vs. CsA, p=0.078 vs. leflunomide). No detectable smooth muscle proliferation was seen, and only scattered interstitial mononuclear cell infiltration and minimal myocardial fibrosis were observed. These results demonstrate that leflunomide combined with CsA caused a dramatic reversal of chronic rejection, returning histologic scores to near normal. The combination treatment reversed the process of arterial intimal thickening in the cellular infiltrating phase, prevented intimal smooth muscle proliferation, and reduced interstitial mononuclear cell infiltration.

Figure 1:
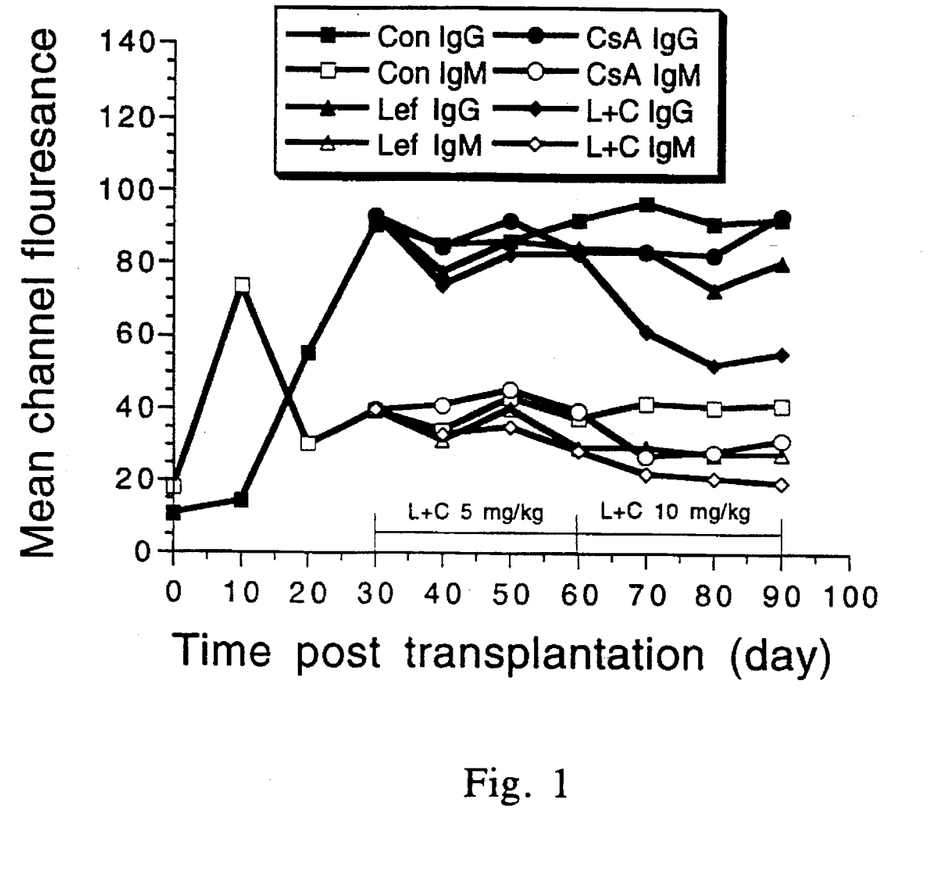
FIG. 1 shows IgM and IgG titres observed in the chronic rejection model of rat cardiac allografts.

IgM titres were also measured in all groups after transplantation. In the control groups, IgM titres reached a peak on day 10 and dropped back to pre-transplantation levels on day 20. IgG titres gradually rose and reached a peak on day 30. These results are displayed in FIG. 1, in which the filled squares, circles, triangles and diamonds represent the IgG levels of the control group, CsA-treated group, leflunomide-treated group, and combination-treated group, respectively, while the open squares, circles, triangles and diamonds represent the IgM levels for those same groups. Without treatment, IgG titres stayed at peak level for another 60 days. Only the combination leflunomide and CsA therapy significantly reduced circulating anti-graft IgM and IgG titres.

TABLE 1

| Group | No. Rats | Treatment From Day 30 to Day 60 | Treatment From Day 60 to Day 90 | Status at Day 90 | Histological Scores |
|---|---|---|---|---|---|
| 1 | 6 | Sacrificed | | | 2.3 ± 0.9 |
| 2 | 6 | None | Sacrificed | | 2.7 ± 1.3 |
| 3 | 5 | None | None | Sacrificed | 3.4 ± 0.9 |
| 4 | 6 | CsA 5 mg/kg | Sacrificed | | 1.6 ± 0.8 |
| 5 | 6 | Lef 5 mg/kg | Sacrificed | | 1.6 ± 0.5 |
| 6 | 6 | CsA 5 mg/kg + Lef 5 mg/kg | Sacrificed | | 0.8 ± 0.3 |
| 7 | 6 | CsA 5 mg/kg | CsA 10 mg/kg | Sacrificed | 2.8 + 1.0 |
| 8 | 6 | Lef 5 mg/kg | Lef 10 mg/kg | Sacrificed | 1.4 ± 0.9 |
| 9 | 6 | CsA 5 mg/kg + Lef 5 mg/kg | CsA 10 mg/kg + Lef 10 mg/kg | Sacrificed | 0.7 ± 0.4 |

EXAMPLE 2

Effect of Leflunomide Alone or with Cyclosporine A on Rejection of Concordant hamster to Rat Cardiac Xenografts This experiment explored the effect of leflunomide alone or in combination with Cyclosporine A (CsA) on rejection of cardiac xenografts in a concordant xenotransplantation model using Golden Syrian hamsters as donors and Lewis (LEW) rats as recipients. In this model, the heart is rejected within 3–4 days, and treatment with drugs such as CsA extends survival for only a few days. The fundamental design of this experiment was to determine a dose response curve using leflunomide as monotherapy, CsA as monotherapy, and both used as combination therapy. End points used to assess efficacy were duration of time to rejection, mortality, histologic differences among the treatment groups, and donor specific antibody responses.

Male LEW rats weighing approximately 200 grams and male Golden Syrian hamsters weighing approximately 150 grams (Harlan, Sprague, Dawley, Indianapolis, Ind.) were allowed five to ten days of acclimatization before surgery was performed. Ketamine-xylazine anesthesia was used in all animals and food and water were freely allowed postoperatively.

Heart transplantation was performed according to the technique of Ono et al., *Cardiovasc. Surg.*, 57:225 (1969), in which the donor aorta and pulmonary artery are anastomosed end-to-side to the recipient's aorta and inferior vena cava, respectively. Cardiac xenograft survival was determined by daily palpation, and rejection was considered complete when the impulse was undetectable. CsA, in its intravenous form (Sandimmune, Sandoz Corporation, East Hanover, N.J.) was administered daily by intramuscular injection to the rat hind limbs. Leflunomide (HWA-486, Hoechst AG, Germany) suspended in 1% carboxymethylcellulose was administered by gavage daily. Immunosuppression therapy was started on the day of surgery unless otherwise specified.

The transplanted animals were assigned to one control group and twelve treatment groups, with dosing at 2.5, 5, 10, 15 and 20 mg/kg of leflunomide, and 10 and 20 mg/kg of CsA. In two groups CsA was kept at 10 mg/kg while leflunomide was dosed at 5 or 10 mg/kg. Three additional treatment groups were included in which leflunomide monotherapy was started seven days before transplantation, or two or three days after transplantation. Treatment regimens, graft survival times for each rat within the treatment group, and mean survival times are shown below in Table 2.

Serum samples were obtained from the animals by drawing 0.2 ml of blood from the tail vein at two day intervals, for the first eight days after transplantation, and then at seven day intervals after day 14. Serum samples were stored at −80° C. The anti-donor specific IgM and IgG titers were measured using cervical lymph nodes from hamsters as target cells for flow cytometry. Lymphocytes obtained from the lymph nodes were washed with PBS and suspended at a concentration of $10^7$ cells/ml. Aliquots of 50 µl containing ~5×10$^5$ lymphocytes were incubated with 50 µl of diluted sera (diluted 1:25 in phosphate buffered saline) for 30 minutes at 4° C. and then washed twice in 1 ml of PBS. IgM and IgG antibodies were stained by incubating the washed cells for 30 minutes at 4° C. with 50 µl of PBS containing a mixture of labeled goat antibodies specific for rat IgG and rat IgM (Jackson Immunoresearch Labs, Westgrove, Pa.). After staining, the cells were washed twice, fixed in 1% formalin and analyzed on the BPICS-C flow cytometry (Coulter Company), according to Williams et al., *Transplantation*, 57:1223–1231 (1994).

The graft heart was excised after cessation of heart beat. Part of the heart was snap frozen in liquid nitrogen and stored at −70° C.; the remainder was fixed in formalin and stained with hematoxylin and eosin to determine pathological changes. The frozen tissue was stained for IgM and IgG deposition using ABC Technique according to Hsu et al., *J. Histochem. Cytochem.*, 29:577 (1981).

The results, displayed in Table 2, show that graft survival with leflunomide treatment exceeded that of untreated controls when the dose reached 10 mg/kg. The optimal dose was 15 mg/kg (mean graft survival 76.5±21 days), as lethal toxicity appeared at 20 mg/kg. Commencing leflunomide therapy seven days before transplantation or delaying it until two days after transplantation had no significant effect on length of graft survival. When initiation of leflunomide was delayed until day 3, all animals rejected the graft within 24 hours. CsA alone at 10 mg/kg had no effect on graft survival. At a dose of 20 mg/kg CsA, graft survival, was significantly prolonged in three animals, but all three died of toxicity. The combination of 5 mg/kg of leflunomide and 10 mg/kg of CsA produced a synergistic effect on graft survival. A higher dose of leflunomide (10 mg/kg leflunomide+10 mg/kg CsA) completely controlled rejection but produced toxicity manifested by inanition and anemia. When all immunosuppression was stopped after 90 days (n=8) or 180 days (n=1) of therapy, the grafts were rejected within ten days.

Interstitial hemorrhage, focal vascular thrombosis and myocardial necrosis with sparse polymorphonuclear cellular infiltration, which are characteristic features of concordant xenograft pathology, were seen in rejected grafts from untreated controls and in animals receiving 2.5 mg/kg leflunomide, 5.0 mg/kg leflunomide and 10 mg/kg CsA. Although 15 mg/kg leflunomide monotherapy prolonged graft survival, the histology of these long-term cardiac grafts featured myocardial fibrosis, moderate mononuclear cell infiltration and arterial thickening, consistent with chronic rejection. Animals treated with combined leflunomide and CsA had essentially normal histology, with minimal histologic changes at 90 days. Nine days after complete cessation of immunosuppressive therapy, an infiltrate of mononuclear cells appeared which resembled unmodified acute allograft rejection.

Figure 2:
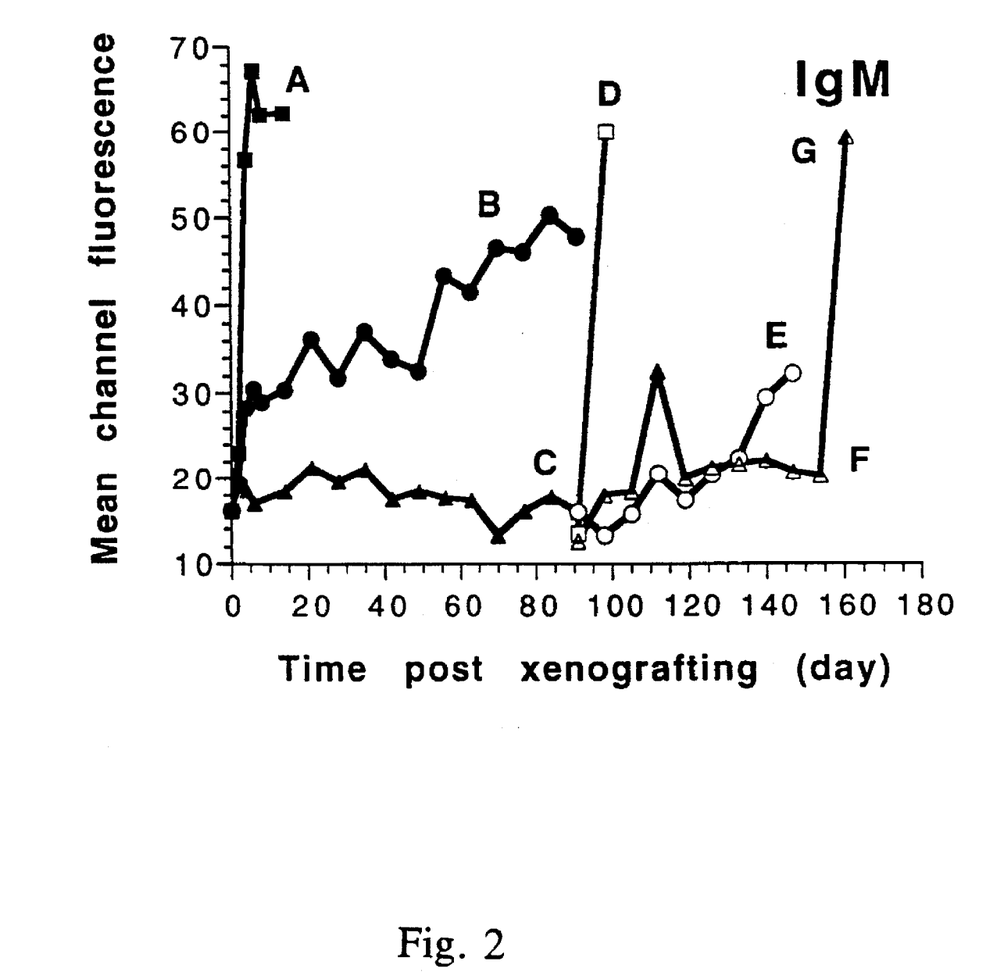
FIGS. 2 and 3 show IgM and IgG levels, respectively, in the hamster to rat cardiac xenotransplant model.
Figure 3:
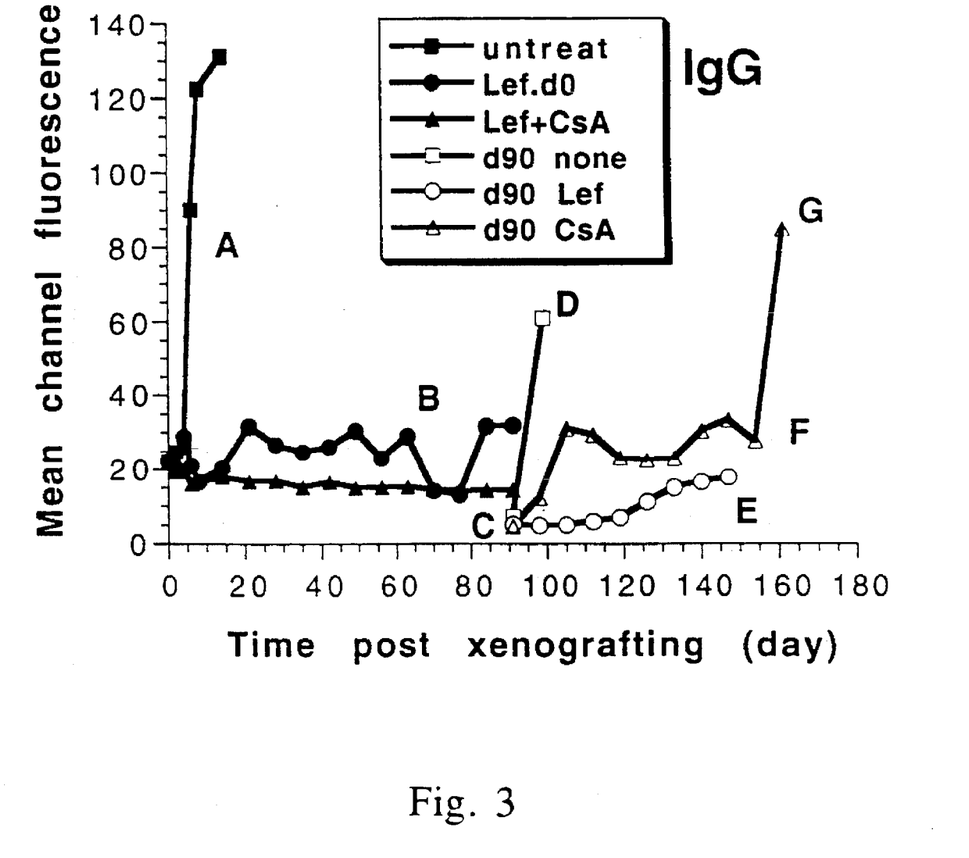

IgM and IgG levels post-transplantation are shown in FIGS. 2 and 3, respectively, in which the filled squares represent levels of untreated controls, the filled circles represent levels after leflunomide therapy commenced at day 0, the filled triangles represent levels after combined leflunomide and CsA therapy started at day 0, the open squares represent complete cessation of combined leflunomide/CsA therapy at day 90, the open circles represent cessation of combined therapy at day 90 with commencement of leflunomide treatment alone at day 90, and the open triangles represent cessation of combined therapy at day 90 with commencement of CsA treatment alone. IgM and IgG titres rose rapidly in untreated controls and in CsA-treated rats. Treatment with leflunomide alone delayed and slowed the rise of IgM titres, but did not completely suppress IgM rise. IgG levels remained at baseline with leflunomide treatment. Under combined therapy with leflunomide and CsA, IgM and IgG titres remained at baseline until treatment was stopped at 90 days. Leflunomide therapy prevented or reversed the cytotoxic antibody titres as measured in the complement-mediated cytotoxicity assay.

These results show that leflunomide as monotherapy is a potent inhibitor of xenorejection, but that even at high doses causing toxicity, it is unable to totally control xenograft rejection. Combined with Cyclosporine A, however, a modest dose of leflunomide (5 mg/kg) provides complete control of all detectable humoral and cellular reactivity. Earlier work with the hamster to rat cardiac xenograft model suggested that drugs whose principal. mode of action is control of T-cell activation (CsA and FK-506) have a limited effect on xenograft survival even at lethal doses. Drugs with substantial B-cell activity (Cytoxan) can completely control rejection of xenografts, but the required dose also is in the lethally toxic range. These observations suggest that both T-cell and B-cell populations independently attack the xenograft and that control of both is required for success. The ability of leflunomide to produce significantly improved xenograft survival as monotherapy compared to other drugs may be due to its effect on both T-cell and B-cell function. It was observed that the total suppression of xeno-antibody production in the group receiving both leflunomide and CsA was accompanied by total control of rejection and indefinite survival.

TABLE 2

| Grp | No | Treatment | Day Began | Graft Survival for Each Subject | Mean Survival ± SD |
|---|---|---|---|---|---|
| 1 | 9 | None | 0 | 3,4,4,4,4,4,4,4,4 | 3.9 ± 0.3 |
| 2 | 6 | Lef 2.5 mg/kg | 0 | 4,5,5,5,5,6 | 5.0 ± 0.6 |
| 3 | 9 | Lef 5 mg/kg | 0 | 6,6,7,7,7,7,7,8,14 | 7.7 ± 2.5 |
| 4 | 8 | Lef 10 mg/kg | 0 | 19,36,41,42,66,67,79,76 | 52.0 ± 20.2 |
| 5 | 6 | Lef 15 mg/kg | 0 | 57,59,63,75,100,105 | 76.5 ± 21.1 |
| 6 | 8 | Lef 20 mg/kg | 0 | 27$^a$,36$^a$,37$^a$,50$^a$,65,66,100,100 | 58.9 ± 28.1 |
| 7 | 9 | CsA 10 mg/kg | 0 | 4,4,4,4,4,4,4,5,6 | 4.3 ± 0.7 |
| 8 | 7 | CsA 20 mg/kg | 0 | 4,4,5,6,57$^b$,59$^c$,59$^c$ | 27.7 ± 28.7 |
| 9 | 8 | Lef 5 mg/kg & CsA 10 mg/kg | 0 | 90,90,90,90,90,90,90,90 | >90 |
| 10 | 6 | Lef 10 mg/kg & CsA 10 mg/kg | 0 | 49,78,79,103,139$^{de}$,188$^{def}$ | 106.0 ± 50.2 |
| 11 | 4 | Lef 10 mg/kg | −7 | 57,57,58,84 | 64.0 ± 13.3 |
| 12 | 7 | Lef 10 mg/kg | +2 | 40,49,54,55,55,76,77 | 58.0 ± 13.7 |
| 13 | 7 | Lef 10 mg/kg | +3 | 3,3,4,4,4,4,4 | 3.7 + 0.5 |

$^a$Treatment was terminated on day 90 and grafts were rejected on day 99 to 100
$^b$Animals died with minimal histologic changes in graft
$^c$Animals died rejecting graft
$^d$Animals were sick on day 70 and the doses of both drugs were reduced by 50%
$^e$CsA was withdrawn on day 130
$^f$Lef was withdrawn on day 180

EXAMPLE 3

Effect of Leflunomide Alone or with Cyclosporine A on Rejection of Concordant Hamster to Rat Renal Xenografts This experiment explored the effect of leflunomide alone or in combination with Cyclosporine A (CsA) on rejection of renal xenografts in the concordant Golden Syrian hamster-LEW rat xenotransplantation model. Like Example 2, this experiment was also designed to determine a dose response curve using leflunomide as monotherapy, CsA as monotherapy, and both used as combination therapy. End points used to assess efficacy were duration of time to rejection, mortality, and histologic differences among the treatment groups.

Golden Syrian hamsters and LEW rats were maintained as in Example 2, and leflunomide and CsA were administered in the same manner as in Example 2. Renal transplantation was performed using cuffs of aorta and vena cava for vascular anastomosis; the donor ureter bearing a button of bladder was connected to the recipient bladder. Both recipient kidneys were removed at the time of transplantation. Rats with graft loss due to technical causes such as vascular thrombosis and bowel obstruction were excluded from the study, leaving 48 recipients assigned to eight treatment groups. Because of the precarious blood supply to the bladder patch and distal ureter, chronic partial urinary obstruction producing tubular dilatation was a common event and complicated the interpretation of both survival data and tubular pathology.

Leflunomide monotherapy was dosed at 2.5, 5, 10 and 15 mg/kg. CsA monotherapy at 10 mg/kg was given to one group. Two groups were given combination therapy of leflunomide 5 mg/kg with CsA 5 mg/kg, and leflunomide 5 mg/kg with CsA 10 mg/kg. Serum creatinine was measured at 7 days and 21 days. Rejection was defined as death of the animal from uremia with histology consistent with immune-mediated injury.

At the death of the and real, the kidney graft was removed, fixed in formalin, and stained with hematoxylin and eosin to determine the extent of pathological change. IgG and IgM staining was also done on formalin-fixed tissue, using ABC Technique as for Example 2.

The treatment regimes, individual survival times for each animal, mean survival times, and measured creatinine are shown in Table 3 below. Untreated control animals died at approximately day 5 from uremia. Administration of 2.5 mg/kg or 5 mg/kg leflunomide (groups 2 and 3) did not significantly increase survival time and did not significantly alter histopathology compared to controls, although mean serum creatinine values were slightly reduced. At 10 mg/kg and 15 mg/kg (groups 4 and 5), however, leflunomide produced a statistically significant improvement in survival, and the histology did not show significant rejection. Mean creatinine values were 1.6 and 1.2 respectively. The cause of death in the animals receiving an appropriate dose of leflunomide was not due to kidney damage in most of the animals, since terminal serum creatinine was less than 2.5. In contrast, CsA monotherapy at 10 mg/kg (group 6) had no effect on survival, and animals died with uremia and severe glomerulitis.

The combination of 10 mg/kg of CsA and 5 mg/kg of leflunomide (group 7) produced a quite significant improvement in survival, with essentially no evidence of kidney graft rejection at necropsy. The cause of death in two animals was probably related to infection in the transplant due to partial obstruction; two others had bladder obstruction from debris within the bladder, and the fifth had no recognizable cause of death. The sixth animal died when drugs were stopped 99 days after transplantation and had a well-healed, non-obstructed urinary system. In this group, neither the serum creatinine values nor the graft histology suggested xenograft rejection. Combination therapy, but not monotherapy with either drug, also consistently prevented IgG and IgM antibody deposition in the kidney.

The survival of animals treated with leflunomide or leflunomide plus CsA was superior to previous reports in the literature but shorter than that of cardiac xenograft recipients receiving the same drugs. However, this may be because the renal xenotransplant model may be more sensitive to rejection. In this model, unlike the heterotopic heart transplant model, survival of the animal is totally dependent on xenograft kidney function, which is reduced because hamster renal clearance is 20–25% of normal rat clearance. The kidney is also particularly sensitive to the deposition of immune complexes. Furthermore, this renal transplant model may be more prone to infection.

No other single drug or combination of drugs has permitted long-term survival in the hamster to rat renal xenograft transplant model; there have been no previous published reports that any therapy has extended survival for more than a few days. Thus, the demonstrated efficacy of therapy with leflunomide alone or in combination with another immunosuppressive agent, CsA, is particularly unexpected in this model.

TABLE 3

| Grp. | No | Treatment | Graft Survival for Each Subject | Mean Survival ± S.D. | Mean Creatinine Day 7 | Mean Creatinine Day 21 |
|---|---|---|---|---|---|---|
| 1 | 7 | None | 4,4,4,5,5,5,6 | 4.7 ± 0.8 | — | — |
| 2 | 6 | Lef 2.5 mg/kg* | 7,7,7,8,10,12 | 8.5 ± 2.1 | 3.6 | — |
| 3 | 6 | Lef 5.0 mg/kg | 4,5,5,9,9,10 | 7.0 ± 2.6 | 2.7 | |
| 4 | 5 | Lef 10 mg/kg* | 9,9,14,26,27 | 17.0 ± 8.9 | 1.6 | |
| 5 | 6 | Lef 15 mg/kg* | 8,5,9,16,17,24 | 13.2 ± 7.1 | 1.2 | |
| 6 | 6 | CsA 10 mg/kg | 4,4,5,5,6,6 | 5.0 ± 0.9 | — | |
| 7 | 6 | CsA 10 mg/kg** + Lef 5 mg/kg | 16,17,30,31,33, 90 | 36 ± 27.4 | 0.6 | 1.2 |

*p < 0.05 compared to controls using the Breslow-Mantel Cox test.
**The combination of Lef and CsA was synergistic by Cox Proportional Hazards analysis.

EXAMPLE 4

Effects of Leflunomide in Combination With Rapamycin on Lymphocyte Proliferation in a One-way Mixed Lymphocyte Reaction The effect of varying concentrations of leflunomide product (A771726, Hoechst AG Werk Albert, Wiesbaden, Germany) in combination with varying concentrations of rapamycin (Wyeth-Ayerst Research, Rouses Point, N.Y.) was evaluated in a one-way mixed lymphocyte reaction (MLR) performed according to Kahan et al., *Transplantation*, 51:232 (1991). Briefly, human peripheral blood lymphocytes ($2\times10^5$ per well) were incubated with an equal number of gamma-irradiated, allogeneic peripheral blood lymphocytes for 5 days in the presence of varying concentrations of leflunomide and rapamycin. The lymphocytes were then incubated for 16 to 20 hours with 1 µCi/well of $^3$H-thymidine. The amount of $^3$H-thymidine uptake was measured, and the percent inhibition of proliferation by each drug or drug combination was calculated. Data from two trials appear below in Tables 4 and 5. These results show that leflunomide interacts with rapamycin to effect greater inhibition of proliferation in MLR, with especially strong interaction at lower drug concentrations, indicating that leflunomide may be used in combination with rapamycin at significantly reduced doses to achieve clinically relevant levels of immunosuppression with reduced toxicities.

TABLE 4

% Inhibition of Lymphocyte Proliferation
By Rapamycin (Rapa) and Leflunomide (Lef)
in One-Way Mixed Lymphocyte Reaction

|  | 0.00 µM Lef | 12.50 µM Lef | 25.00 µM Lef | 50.00 µM Lef |
| --- | --- | --- | --- | --- |
| 0.00 nM Rapa | 0.00 | 15.19 | 37.35 | 56.71 |
| 0.010 nM Rapa | 27.12 | 44.67 | 57.43 | 65.55 |
| 0.050 nM Rapa | 38.78 | 53.75 | 61.35 | 73.94 |
| 0.100 nM Rapa | 57.42 | 71.99 | 75.09 | 79.89 |
| 1.00 nM Rapa | 89.25 | 89.02 | 92.79 | 92.43 |

TABLE 5

% Inhibition of Lymphocyte Proliferation
By Rapamycin (Rapa) and Leflunomide (Lef)
in One-Way Mixed Lymphocyte Reaction

|  | 0.00 µM Lef | 12.50 µM Lef | 25.00 µM Lef | 50.00 µM Lef |
| --- | --- | --- | --- | --- |
| 0.00 nM Rapa | −8.72 | 21.84 | 38.40 | 68.63 |
| 0.010 nM Rapa | 4.78 | 33.81 | 56.63 | 67.39 |
| 0.050 nM Rapa | 37.75 | 53.89 | 59.10 | 61.90 |
| 0.100 nM Rapa | 51.71 | 55.28 | 52.21 | 62.07 |
| 1.00 nM Rapa | 80.83 | 83.93 | 80.66 | 85.28 |

Numerous modifications and variations in the practice of the invention are expected to occur to those skilled in the art upon consideration of the foregoing description of the presently preferred embodiments thereof. For example, while the foregoing examples relate to combinations of leflunomide with cyclosporine A, combinative therapy involving leflunomide and other immunosuppressive agents such as FK506, rapamycin, and corticosteroids is contemplated. Consequently, the only limitations which should be placed upon the scope of the present invention are those which appear in the appended claims.

What is claimed is:

1. A method for controlling or reversing the development of obliterative fibrosis of allograft arteries characteristic of chronic rejection in a transplantation patient, said method comprising administering to a patient suffering from chronic rejection of an allograft a therapeutically effective amount of leflunomide product.

2. The method of claim 1 wherein the leflunomide product is N-(4-trifluoromethylphenyl)-5-methylsiloxazol-4-carboxamide.

3. The method of claim 1 wherein the leflunomide product is N-(4-trifluoromethylphenyl)-2-cyano-3-hydroxycrotonamide.

4. The method of claim 1 wherein the amount of leflunomide product administered is from 0.1 to 80 mg/day.

5. The method of claim 1 wherein the allograft is a skin, heart, lung, kidney, liver or pancreatic islet cell allograft.

6. The method of claim 1 further comprising administering to the patient therapeutically effective amounts of one or more immunosuppressive agents selected from the group consisting of Cyclosporine A, FK506, rapamycin and corticosteroids.

7. The method of claim 6 wherein the leflunomide product is N-(4-trifluoromethylphenyl)-5-methylsiloxazol-4-carboxamide.

8. The method of claim 6 wherein the leflunomide product is N-(4-trifluoromethylphenyl)-2-cyano-3-hydroxycrotonamide.

9. A method for controlling or reversing the development of obliterative fibrosis of allograft arteries characteristic of chronic rejection in a transplantation patient, said method comprising administering to a patient suffering from chronic rejection of an allograft a therapeutically effective amount of leflunomide product and further comprising administering to the patient a therapeutically effective amount of Cyclosporine A.

10. The method of claim 9 wherein the amount of leflunomide product administered is from 0.1 to 80 mg/day and the amount of Cyclosporine A administered is from 0.1 to 12 mg/kg/day.

11. The method of claim 6 wherein the allograft is a skin, heart, lung, kidney, liver or pancreatic islet cell allograft.

* * * * *

UNITED STATES PATENT AND TRADEMARK OFFICE
CERTIFICATE OF CORRECTION

PATENT NO. : 5,624,946
DATED : April 29, 1997
INVENTOR(S) : Williams

It is certified that error appears in the above-indentified patent and that said Letters Patent is hereby corrected as shown below:

At Col. 5, line 19, "precinisolone" should be --prednisolone--.

At Col. 6, line 7, "fernoral" should be --femoral--.

At Col. 7, line 63, "fernoral" should be --femoral--.

At Col. 8, line 9, "fernoral" should be --femoral--.

At Col. 12, line 24, "or" should be --of--.

At Col. 14, line 4, "clay" should be --day--.

At Col. 15, line 19, "hamster" should be --Hamster--.

At Col. 16, line 17, "tilers" should be --titers--.

At Col. 16, line 21, "cells/mi." should be --cells/ml.--.

At Col. 16, line 26, "4° C." should --4°C--.

At Col. 16, line 35, "70° C." should be --70°C--.

UNITED STATES PATENT AND TRADEMARK OFFICE
CERTIFICATE OF CORRECTION

PATENT NO. : 5,624,946
DATED : April 29, 1997
INVENTOR(S) : Williams

It is certified that error appears in the above-indentified patent and that said Letters Patent is hereby corrected as shown below:

At Col. 17, line 59, "principal." should be --principal--.

At Col. 19, line 5, "and real," should be --animal,--.

At Col. 22, claim 2, "methylsiloxazol" should be --methylisoxazol--.

At Col. 22, claim 7, "methylsiloxazol" should be --methylisoxazol--.

Signed and Sealed this

Fourth Day of August, 1998

Attest:

BRUCE LEHMAN

Attesting Officer

Commissioner of Patents and Trademarks